United States Patent
Kolen et al.

(10) Patent No.: US 10,251,625 B2
(45) Date of Patent: Apr. 9, 2019

(54) EXAMINATION SYSTEM WITH MULTIPLE ULTRASOUND TRANSDUCERS

(71) Applicant: KONINKLIJKE PHILIPS N.V., Eindhoven (NL)

(72) Inventors: Alexander Franciscus Kolen, Eindhoven (NL); Godefridus Antonius Harks, Ruen (NL); Steven Antonie Willem Fokkenrood, S'Hertogenbosch (NL); Szabolcs Deladi, Veldhoven (NL); Darrell L. Rankin, Milpitas, CA (US); David L. McGee, San Miguel, CA (US)

(73) Assignees: Koninklijke Philips N.V., Eindhoven (NL); Boston Scientific Scimed, Inc., Maple Grove, MN (US)

(*) Notice: Subject to any disclaimer, the term of this patent is extended or adjusted under 35 U.S.C. 154(b) by 60 days.

(21) Appl. No.: 14/362,364

(22) PCT Filed: Nov. 12, 2012

(86) PCT No.: PCT/IB2012/056356
§ 371 (c)(1),
(2) Date: Jun. 2, 2014

(87) PCT Pub. No.: WO2013/084094
PCT Pub. Date: Jun. 13, 2013

(65) Prior Publication Data
US 2014/0343426 A1    Nov. 20, 2014

Related U.S. Application Data

(60) Provisional application No. 61/568,212, filed on Dec. 8, 2011.

(51) Int. Cl.
*A61B 8/00* (2006.01)
*A61B 8/12* (2006.01)
(Continued)

(52) U.S. Cl.
CPC ........... *A61B 8/463* (2013.01); *A61B 8/0841* (2013.01); *A61B 8/12* (2013.01); *A61B 8/4254* (2013.01);
(Continued)

(58) Field of Classification Search
USPC ....................................... 600/440
See application file for complete search history.

(56) References Cited

U.S. PATENT DOCUMENTS 4,841,977 A * 6/1989 Griffith .................... A61B 8/12
29/25.35
7,706,646 B2  4/2010 Wang et al.
(Continued)

FOREIGN PATENT DOCUMENTS

CN  101385654 A  3/2009
CN  101437455 A  5/2009
(Continued)

*Primary Examiner* — Joel F Brutus

(57) ABSTRACT

To sum up, the present invention relates to an examination system 1301 for examining an associated tissue sample 1302, where the examination system comprises an interventional device 1320 which comprises a plurality of ultrasound transducers 306a-c and wherein the different ultrasound transducers are arranged to obtain images of different regions of an associated tissue sample, and wherein the examination system furthermore comprises a display device 1351 arranged for showing the images so that each of their positions corresponds to the corresponding positions of the different adjacent tissue sample regions in the adjacent associated tissue sample. A possible advantage of the system may be that relevant information regarding the associated tissue sample is conveyed to an observer in a fast an intuitive manner.

14 Claims, 10 Drawing Sheets

(51) Int. Cl.
*A61B 8/08* (2006.01)
*A61B 10/04* (2006.01)

(52) U.S. Cl.
CPC ............ *A61B 8/445* (2013.01); *A61B 8/4477* (2013.01); *A61B 8/4494* (2013.01); *A61B 8/462* (2013.01); *A61B 8/5223* (2013.01); *A61B 8/5246* (2013.01); *A61B 10/04* (2013.01); *A61B 8/429* (2013.01); *A61B 8/486* (2013.01); *A61B 8/5253* (2013.01); *A61B 2010/045* (2013.01)

(56) References Cited

U.S. PATENT DOCUMENTS

| | | |
|---|---|---|
| 8,755,860 B2 | 6/2014 | Sauray et al. |
| 2003/0229286 A1 | 12/2003 | Lenker |
| 2004/0006266 A1* | 1/2004 | Ustuner .................. A61B 8/08 600/407 |
| 2005/0124888 A1* | 6/2005 | Jjt Rein ............... A61B 8/0833 600/443 |
| 2006/0253028 A1* | 11/2006 | Lam ........................ A61B 8/12 600/459 |
| 2007/0167801 A1* | 7/2007 | Webler ................ G06F 19/3437 600/459 |
| 2009/0024034 A1 | 1/2009 | Moreau-Gobard et al. |
| 2009/0069679 A1 | 3/2009 | Hibi |
| 2009/0148012 A1* | 6/2009 | Altmann ............... A61B 6/5247 382/128 |
| 2009/0177111 A1* | 7/2009 | Miller ................... A61B 5/053 600/547 |
| 2010/0174189 A1 | 7/2010 | Abraham |
| 2012/0004547 A1 | 1/2012 | Harks et al. |

FOREIGN PATENT DOCUMENTS

| | | |
|---|---|---|
| CN | 102085117 A | 6/2011 |
| EP | 2036500 | 3/2009 |
| EP | 2338431 A1 | 6/2011 |
| JP | 2003135459 A | 5/2003 |
| RU | 2424769 A | 12/2010 |
| WO | WO2006113857 | 10/2006 |
| WO | WO2009018085 | 2/2009 |
| WO | WO2010138448 | 12/2010 |

* cited by examiner

EXAMINATION SYSTEM WITH MULTIPLE ULTRASOUND TRANSDUCERS

CROSS-REFERENCE TO PRIOR APPLICATIONS

This application is the U.S. National Phase application under 35 U.S.C. § 371 of International Application Serial No. PCT/IB2012/056356, filed on Nov. 12, 2012, which claims the benefit of U.S. Application Ser. No. 61/568,212, filed on Dec. 8, 2011. These applications are hereby incorporated by reference herein.

FIELD OF THE INVENTION

The present invention relates to the field of examination systems, in particular, the present invention relates to examination systems comprising interventional devices with multiple ultrasound transducers, and a corresponding method, computer program product, and use of such system.

BACKGROUND OF THE INVENTION

Examination systems comprising interventional devices with ultrasound transducers for providing information from the interior of adjacent tissue samples, such as anatomical regions, e.g., the structure of a heart, may suffer from providing an overload of information. This may be critical in situations of use where important decisions have to be made within a limited timeframe. In order to prevent the overload of information, the amount of information may be reduced such as by discarding information. However, this might lead to a loss of relevant information. It would certainly improve the situation if it were possible to utilize the obtained information in an improved manner.

The reference WO 2010/138448 A1 describes a catheter assembly which includes a catheter and a delivery element. The catheter has a distal end with a distal tip, a proximal end, and a longitudinal length, the catheter includes a body that defines a central lumen extending along the catheter to the distal end. The catheter also includes a forward-facing transducer array disposed at the distal tip of the catheter. The transducer array is configured and arranged for transforming applied electrical signals to acoustic signals and also for transforming received echo signals to electrical signals. At least one catheter conductor is electrically coupled to the transducer array and extends along the catheter. The delivery element is disposed in the lumen of the catheter.

An improved examination system for examining an associated tissue sample would be advantageous, and in particular an examination system which enables obtaining and utilizing large amounts of information from an associated tissue sample in an improved, more efficient, simple, fast and/or reliable manner would be advantageous.

SUMMARY OF THE INVENTION

In particular, it may be seen as an object of the present invention to provide an examination system that solves the above mentioned problems of the prior art concerning obtaining and utilizing large amounts of information from an associated tissue sample in an improved, more efficient, simple, fast and/or reliable manner.

It is a further object of the present invention to provide an alternative to the prior art.

Thus, the above described object and several other objects are intended to be obtained in a first aspect of the invention by providing an examination system for examining an associated tissue sample, the examination system comprising
an interventional device comprising:
a plurality of ultrasound transducers, wherein different ultrasound transducers within the plurality of ultrasound transducers are arranged to obtain ultrasound information packages from spatially different tissue sample regions when the associated tissue sample is placed adjacent the plurality of ultrasound transducers,
a display device arranged for receiving and visualizing the ultrasound information packages in spatially different ultrasound display regions on the display device,
wherein the relative spatial positions of the different ultrasound display regions match the corresponding relative spatial positions of the different adjacent tissue sample regions.

The invention is particularly, but not exclusively, advantageous for obtaining ultrasound information packages from spatially different tissue sample regions and for visualizing the ultrasound information packages in a manner wherein the relative spatial positions of the different ultrasound display regions match the corresponding relative spatial positions of the different adjacent tissue sample regions, which has the effect that an observer of the display device is presented in a very intuitive manner with information from the different adjacent tissue sample regions. Thus, the observer need not toggle through different images or constantly having to keep in mind which portion of the display device corresponds with which part of the associated tissue sample.

The invention addresses the issue that the position of, e.g., M-mode ultrasound images on, e.g., a screen to be seen by a person during, e.g., an ablation intervention does not correspond with the position of the ultrasound transducers in the end of the interventional device, such as in the catheter tip. The present invention proposes to overcome this problem by visually intuitively position the location of the generated images corresponding to the actual location of the transducers in the interventional device. Thus, by taking the relative spatial positions of the different adjacent tissue sample regions (which depend on technical features, such as technical features of the interventional device, such as the positions and orientations of the ultrasound transducers on the interventional device) into account, the technical problem of optimizing the handling of the interventional device may be addressed. In a particular embodiment, the display device also comprises an input for receiving the relative spatial positions of the different adjacent tissue sample regions.

It is noticed, that an examination system according to the invention may further be favorable in that it clearly reflects a status or condition of the system, since the different ultrasound display regions (when arranged according to the invention) may reflect a status or condition of the system to the observer.

The gist of the invention may be described as taking the information from all the ultrasound transducers in the plurality of ultrasound transducers and presenting this information in an intuitive way, so that a recipient of the information may in a very fast and correspondingly intuitive way be presented with the relevant information. In that way, neither the examination system nor the recipient need to spend time or resources for selecting which information need not be presented. It may thus be seen as a basic insight of the invention, that valuable information may be lost if information from one or more ultrasound transducers is not presented, for example if a computer algorithm has decided not to show information from a particular ultrasound transducer or a human recipient has selected not to show information from a particular ultrasound transducer, such as by toggling between images to be shown and thus discarding information. It may also be seen as an insight underlying the present invention, that if the information from the different adjacent tissue regions is presented in an intuitively appropriate manner, then the human vision system is likely to be superior for detecting relevant information, hence a system according to the present invention may in an efficient way enable exploiting the superb human vision and image analysis capabilities.

Furthermore, it may also be seen as the gist of the invention, that additional information may be extracted from the ultrasound information packages by representing the ultrasound information packages according to the invention. The invention might actually provide new information to the observer, because the observer can link tissue features seen in the individual ultrasound information packages in spatially different ultrasound display regions with each other. In other words: Not only can the system, method and use according to the invention potentially enable that more information is provided to the user (since no information need to be discarded in order to not risk overloading the observer with information which the observer cannot interpret), but the system, method and use furthermore via the technical features of the system, method and use according to the independent claims appended to the description—may enable the observer to identify features in the combination of the ultrasound information packages, which would otherwise have appeared irrelevant when identified in the individual ultrasound information packages.

Still further, an observer may possibly utilize the information from individual ultrasound information packages depicted in spatially different ultrasound display regions in order to make a qualified guess regarding information in regions which are not probed. Thus, the invention might enable the observer to interpolate between adjacent ultrasound display regions, so as to obtain additional information.

By 'an associated tissue sample' is understood a portion of a tissue, such as animal tissue, such as tissue in a dead or living body of a human or an animal. Tissue sample may be interchangeably referred to as 'anatomical region'.

An 'interventional device' is generally known in the art, and may include any one of the non-exhaustive list comprising a catheter, a needle, a biopsy needle or an endoscope.

It is understood that 'ultrasound transducers' are known in the art as elements which upon actuation may emit and/or receive ultrasound signals. The actuation may be an applied voltage. An ultrasound transducer adapted to receive ultrasound signals may convert a received ultrasound signal into a voltage, such as a time varying voltage. By a plurality of ultrasound transducers is understood an integer larger than one, such as 2, 3, 4, 5, 6, 7, 8, 9 or more ultrasound transducers.

By 'ultrasound information packages' is understood information obtained via the ultrasound transducers, such as a received intensity as a function of time, such as a received intensity as a function of time for a particular period in time for a particular spatial region, such as the received ultrasound signal being assumed to be indicative of a particular spatial region of the adjacent associated tissue sample.

By an ultrasound transducer or a plurality of ultrasound transducers being 'arranged to obtain ultrasound information packages' is understood that the ultrasound transducer or the plurality of ultrasound transducers is arranged so that ultrasound signals which carry information from an adjacent associated tissue sample is received by the ultrasound transducer or the plurality of ultrasound transducers and converted into a readable signal, such as a voltage signal. In a specific embodiment, an ultrasound signal is emitted from an ultrasound transducer, reflected off the adjacent associated tissue sample at one or more positions and received by the same or another ultrasound transducer.

By 'spatially different tissue sample regions' is understood different regions, such as different volumes, such as non-identical, overlapping or non-overlapping volumes of the associated tissue sample, which different regions are not having the same position in space.

By 'a display device' is understood any device capable of displaying information derived from the 'spatially different tissue sample regions', where the device is capable of being spatially resolvable into different ultrasound display regions. In particular embodiments, the display device may be a computer screen, such as a computer monitor, or a set of light emitting units, such as light emitting diodes spatially arranged to match corresponding positions of different adjacent tissue sample regions.

By 'for receiving and visualizing the ultrasound information packages' is understood that the information in the ultrasound information packages is received, such as received by an analog-to-digital converter (ADC) and that the information is visualized, such as imaged as a grey tone image, or analyzed and visualized as a one-dimensional value, such as the information being analyzed and converted into a level of tissue contact which may be visualized simply by a light intensity and/or color.

The phrase 'the relative spatial positions of the different ultrasound display regions match the corresponding relative spatial positions of the different adjacent tissue sample regions' will be further explained in the following. The different adjacent tissue sample regions each have a position (in the associated tissue sample), and since there is more than one adjacent tissue sample region, each of their positions may be defined with respect to the others. In analytical geometry wording, the positions of each of the adjacent tissue sample regions may be defined by a vector in a coordinate system, such as a coordinate system being fixed to the interventional device and/or the associated tissue sample. The coordinate system may be, e.g., two-dimensional. Thus, a first set of vectors may describe the positions of the adjacent tissue sample regions. Similarly, a second set of vectors may describe the ultrasound display regions. By 'match' is understood, that the spatial relations, in terms of length and orientation, between the vectors in each set is substantially identical.

The invention encompasses embodiments where the second set of vectors has been stretched, such as scaled differently in different directions, such as the difference in stretch being within 0-50%, such as within 0-40%, such as within 0-30%, such as within 0-20%, such as within 0-10%.

The invention encompasses embodiments where one or more individual vectors in the second set of vectors differ in length with respect to a length of a corresponding vector in a second set of vectors having exactly the same spatial relations as the first set of vectors, such as having a difference in length being within 0-50%, such as within 0-40%, such as within 0-30%, such as within 0-20%, such as within 0-10%.

The invention encompasses embodiments where one or more individual vectors in the second set of vectors is angled, such as slightly angled, with respect to an angle of the corresponding vector in a second set of vectors having exactly the same spatial relations as the first set of vectors, such as being angled within 0-45 degrees, such as within 0-30 degrees, such as within 0-20 degrees, such as within 0-10 degrees, such as within 0-5 degrees, such as within 0-1 degrees.

In a particular embodiment, the relative orientation of each of the different ultrasound display regions around an axis through the middle of the ultrasound display region matches the relative orientation of the adjacent tissue sample regions around their respective axes. This is particularly relevant if the ultrasound display regions are displaying images, such as two-dimensional images.

In a particular embodiment, the relative orientation of each of the different ultrasound display regions around an axis through the middle of the ultrasound display region match the relative orientations of the adjacent tissue sample regions around their respective axes within 0-90 degrees, 0-60 degrees, 0-45 degrees, such as within 0-30 degrees, such as within 0-20 degrees, such as within 0-10 degrees, such as within 0-5 degrees, such as within 0-1 degrees. Having matching rotations will have the advantage that images from, e.g., different sides of the interventional device may otherwise appear to be tilted or turned upside-down with respect to one another.

It is also understood, that the position and orientation of the plurality of ultrasound transducers may be substantially identical to the relative spatial positions of the different adjacent tissue sample regions, and that 'the relative spatial positions and/or orientations of the different adjacent tissue sample regions' may be used interchangeably with 'relative spatial positions and/or orientations of the ultrasound transducers in the plurality of ultrasound transducers'.

In another embodiment the invention further relates to an examination system wherein the interventional device further comprises a plurality of tissue contact sensors being placed on spatially distributed tissue contact sensor positions and
arranged to obtain tissue contact information packages which are indicative of tissue contact between the interventional device and the associated tissue sample at the tissue contact sensor positions.

It is noted that in a particular embodiment, the tissue contact sensors may be embodied by the ultrasound transducers themselves, wherein images obtained with the ultrasound transducers may be analyzed so as to extract the degree of tissue contact between each of the ultrasound transducers and tissue. In other words, the level of tissue contact is derived from the ultrasound images. In another embodiment the invention further relates to an examination system further comprising a processing unit, such as an image analysis unit, arranged for determining a level of tissue contact between an ultrasound transducer from the corresponding information package. For example the ultrasound information package may be converted to an image by a processor which is also arranged for carrying out image analysis in order to determine a level of tissue contact between tissue and ultrasound transducer.

In a further embodiment the invention further relates to an examination system wherein the display device is arranged for receiving and visualizing the tissue contact information packages in spatially different tissue contact display regions of the display device, and wherein the relative spatial positions of the different tissue contact display regions are similar to the relative spatial positions of the tissue contact sensor positions. An advantage of this may be that it enables visualizing where the interventional device is in tissue contact in an intuitive manner. Thus, an observer need not constantly having to keep in mind which tissue contact display regions corresponds with which part of the associated tissue sample.

In another embodiment the invention further relates to an examination system further comprising a processing unit, such as an image analysis unit, arranged for identifying predetermined features in the information packages, such as a cardiac wall or a lesion. For example the ultrasound information packages may be converted to images by a processor which is also arranged for carrying out image analysis in order to determine particular predetermined features in the images, such as certain reflections, e.g., from a wall of an organ.

In a further embodiment the invention further relates to an examination system wherein the display device is further arranged for indicating the position of any one of the predetermined features on the display. The information of the position of the predetermined features may be conveyed to an observer in an intuitive manner by marking them on the ultrasound display regions, such as by a change of color, a bright or dark line, arrows or the like.

In another embodiment the invention further relates to an examination system wherein the interventional device is any one of an endoscope, a catheter, a biopsy needle. An advantage of having an interventional device may be that it enables obtaining information from within associated tissue samples or hollow entities with a narrow entrance.

In another embodiment the invention further relates to an examination system wherein the plurality of ultrasound transducers comprises at least 3 different ultrasound transducers. In another embodiment the invention further relates to an examination system wherein the plurality of ultrasound transducers comprises at least 4, 5, 6, 7, 8, 9 or more different ultrasound transducers. An advantage of having 3 or more ultrasound transducers may be that a more detailed level of information, such as information with a better spatial or temporal resolution, can be obtained from the associated tissue sample.

In another embodiment the invention further relates to an examination system wherein a coordinate position of at least one ultrasound transducer within the plurality of ultrasound transducers is determined with respect to a fixed coordinate system, such as by means of image analysis, such as by means of optical shape sensing, such as by means of a marker unit. An advantage of this may be that it enables that an observer is provided with information regarding the position of at least one ultrasound transducer, such as a position with respect to a fixed entity, such as the display device or the ground, such as a position with respect to the associated tissue sample.

In a further embodiment the invention further relates to an examination system wherein the spatial positions of the different ultrasound display regions is based on said coordinate position. For example, if the interventional device is rotated, the ultrasound display regions may correspondingly rotate, or if the interventional device is moved up or down, the ultrasound display regions may correspondingly move up or down.

In another embodiment the invention further relates to an examination system wherein the spatially different tissue sample regions are positioned around the interventional device. An advantage of this may be that it enables obtaining information regarding an associated tissue sample being placed around the interventional device. Another advantage may be, that information from a relatively large region of an associated tissue sample may be obtained, since a relatively narrow interventional device equipped with ultrasound transducers for obtaining ultrasound information packages from a plurality of spatially different tissue sample regions being positioned around the interventional device enables yielding information from an associated tissue sample being larger, such as significantly larger than a cross section of the interventional device. In effect, only a small hole in the associated tissue needs to be made in order to obtain information from a large region of the associated tissue sample. In an embodiment, the ultrasound transducers within the plurality of ultrasound transducers are facing outwards with respect to the interventional device, such as arranged for emitting ultrasound signals into spatially different tissue sample regions are positioned around the interventional device and/or receiving ultrasound signals from spatially different tissue sample regions are positioned around the interventional device.

In an embodiment the invention further relates to an examination system wherein the interventional device and the display device are attached to a handle, such as the ultrasound display regions being positioned on different sides of the handle, such as around the handle. An advantage may be that a person operating the interventional device will have the display device placed in a position, namely the handle, where attention is naturally directed. Another advantage may be that it enables integration of parts since the handle and the display device is integrated into a single unit.

In another embodiment the invention further relates to an examination system wherein the spatially different tissue sample regions are non-overlapping. In another embodiment the invention further relates to an examination system wherein the spatially different tissue sample regions are overlapping.

According to a second aspect of the invention, the invention further relates to a method according to the independent method claim.

According to a third aspect of the invention, the invention further relates to a computer program product according to the independent computer program product claim.

According to a fourth aspect of the invention, the invention further relates to use of an examination system according to the first aspect for examining an associated tissue sample.

The first, second, third and fourth aspect of the present invention may each be combined with any of the other aspects. These and other aspects of the invention will be apparent from and elucidated with reference to the embodiments described hereinafter.

BRIEF DESCRIPTION OF THE FIGURES

The system, method, computer program product and use according to the invention will now be described in more detail with regard to the accompanying figures. The figures show one way of implementing the present invention and is not to be construed as being limiting to other possible embodiments falling within the scope of the attached claim set.

DETAILED DESCRIPTION OF AN EMBODIMENT

Embodiments of the present invention are disclosed in the following.

Figure 1:
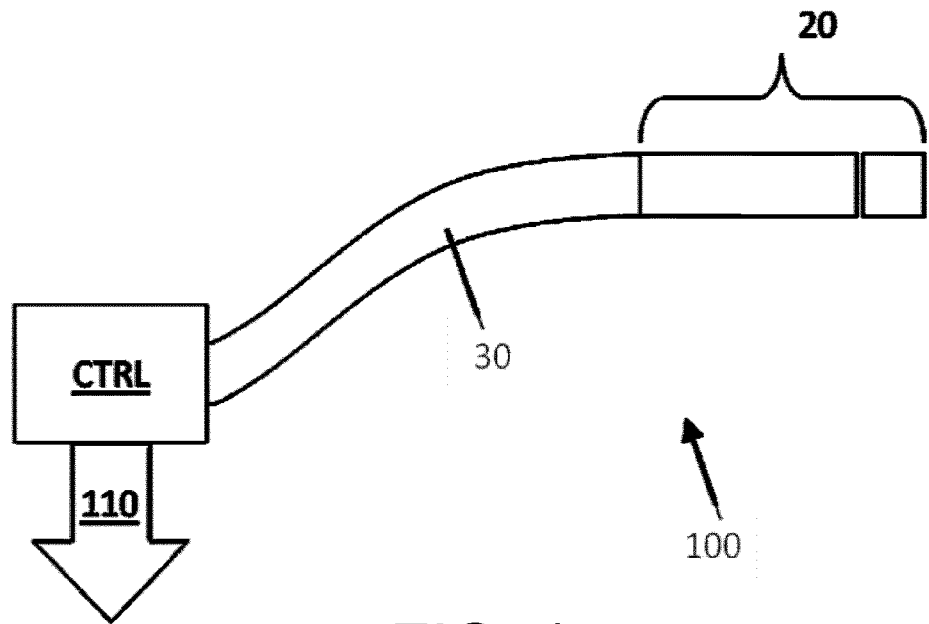
FIG. 1 shows a general system 100 for obtaining information via ultrasound.

FIG. 1 shows a general system 100 for obtaining information via ultrasound, and the particular system depicted is also applicable for performing ablation, the system comprising a controllable energy source for providing energy to the ablation unit and/or the ultrasonic transducer (neither shown in this figure). Additionally, a sample arm 30 is coupled to the energy source, the sample arm having at its distal end an interventional device 20 according to an embodiment of the present invention. The interventional device may include any one of the non-exhaustive list comprising a catheter, a needle, a biopsy needle or an endoscope. It is also contemplated that a plurality of ultrasound transducers could be comprised within the interventional device, and some ultrasound transducers some of which could be only emitting whereas other transducers could be only receiving. The system 100 further comprises a controlling unit (CTRL), arranged to send ultrasound information packages 110 to a display device.

The invention might be used in tissue imaging during use, for example in connection with heart arrhythmias or in oncology, where it is advantageous to obtain images during operation, such as for assessing a risk of impending tissue damage due to a rapid release of bubble energy and thus form a basis for deciding how to operate the ablation unit.

Figure 2:
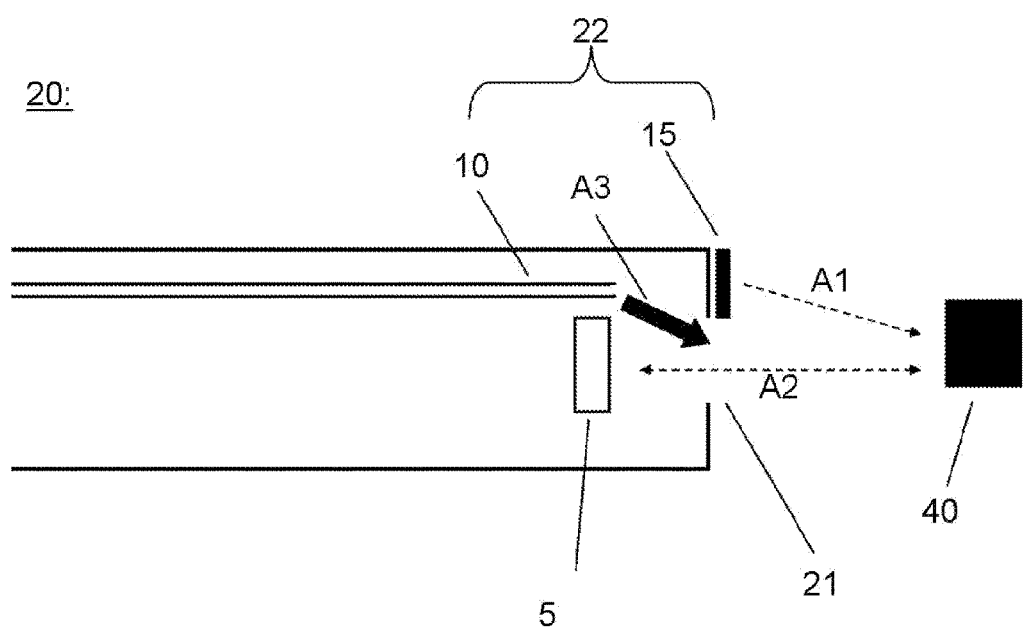
FIG. 2 shows a schematic, cross-sectional drawing of a catheter.

FIG. 2 shows a schematic, cross-sectional drawing of a catheter 20 which is adapted for open-loop irrigated ablation, e.g. RF ablation, of a tissue 40, the catheter 20 having a distal end 22, i.e. the right-hand part of the shown catheter embraced by the bracket, where the distal end comprises an ablation entity 15 adapted for performing ablation of the tissue 40. Note that although in FIG. 2 the ablation entity is depicted as covering only the forward side of the catheter, it may also cover the catheter sidewards. The radiation for performing ablation is schematically shown by dotted arrow A1. The required wiring for energizing and/or controlling the ablation entity is not shown in this figure for clarity. In addition, an irrigation hole 21 is provided. The irrigation fluid is flowing out of a dedicated irrigation fluid conduct 10, e.g. a flexible tube, as indicated schematically by solid arrow A3. The irrigation fluid is functioning as an acoustic coupling medium, which may be defined as a medium substantially transparent to ultrasonic waves, such as a saline solution or water or other similar liquids available to the skilled person implementing the invention.

Further, an ultrasound transducer 5 is positioned in the distal end, the transducer being adapted for transmitting and/or receiving ultrasonic waves as schematically indicated by double-headed dotted arrow A2 in FIG. 2. In the most general form of the invention, the ultrasound transducer is disposed behind (as in this figure) or in the irrigation hole 21 of the catheter 20, so as to allow an irrigation fluid A3 to flow out of the irrigation hole, and so as to allow transmitting and/or receiving the ultrasonic waves through the same irrigation hole 21.

Advantageously, the catheter 20 may be used for open-loop irrigated radio frequency (RF) ablation.

In FIG. 2, there is shown only one ultrasound transducer 5. However, there may be multiple ultrasound transducers present, such as a forward looking ultrasound transducer, such as the depicted ultrasound transducer 5, and one or more sideward looking ultrasound transducers (not shown in FIG. 2).

Figure 3:
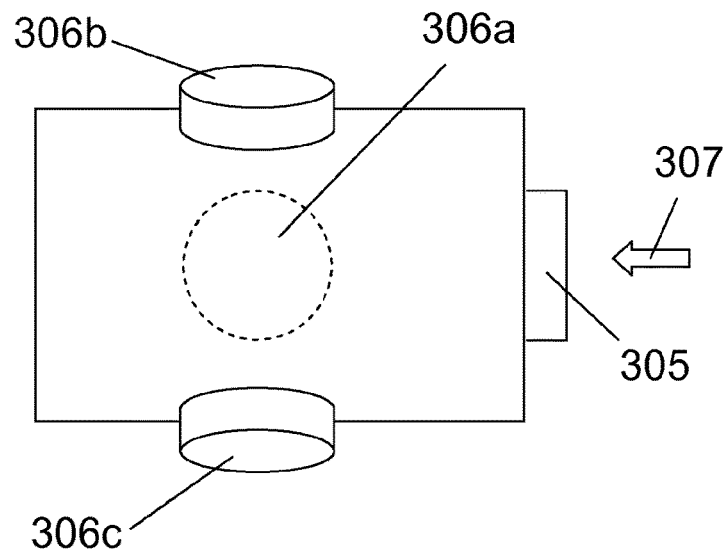
FIGS. 3-5 show side view, end view and perspective view of a distal end of an interventional device.

FIG. 3 shows a side view (as in FIG. 2) of a distal end 322 of an interventional device, with a forward looking ultrasound transducer 305 and three sideward looking ultrasound transducers 306a-c. All ultrasound transducers are mounted on the side of the interventional device, but they could also be mounted within the interventional device (such as shown in FIG. 2) or be integrated in the surface of the interventional device so that a surface of the ultrasound transducers lies substantially flush with a surface of the interventional device. The three sideward looking ultrasound transducers 306a-c are mounted on the surface of the interventional device, and being arranged for emitting and receiving ultrasound signals to/from a direction being orthogonal to a length axis of the interventional device. In this particular embodiment, the interventional device is thus enabled to obtain ultrasound signals from 4 different directions, i.e., a forward direction (being parallel with a length axis of the interventional device) and three sideward directions (being orthogonal to a length axis of the interventional device), each ultrasound transducer being angled approximately 120 degrees around the length axis of the interventional device, with respect to the two other ultrasound transducers.

Figure 4:
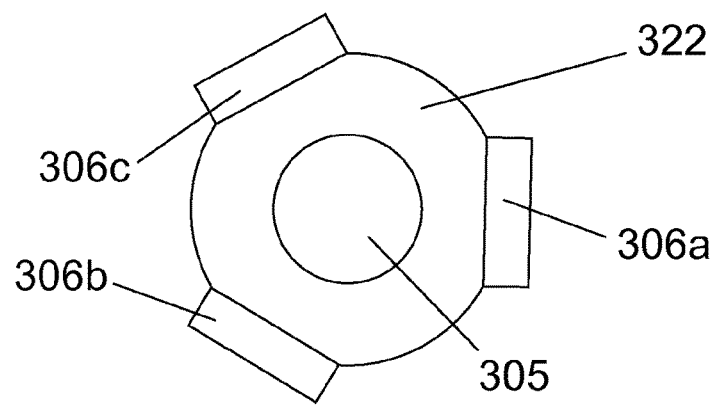

FIG. 4 shows an end view of a distal end 322 of an interventional device, with a forward looking ultrasound transducer 305 and three sideward looking ultrasound transducers 306a-c. The end view is seen in a direction as indicated with arrow 308 in FIG. 3.

Figure 5:
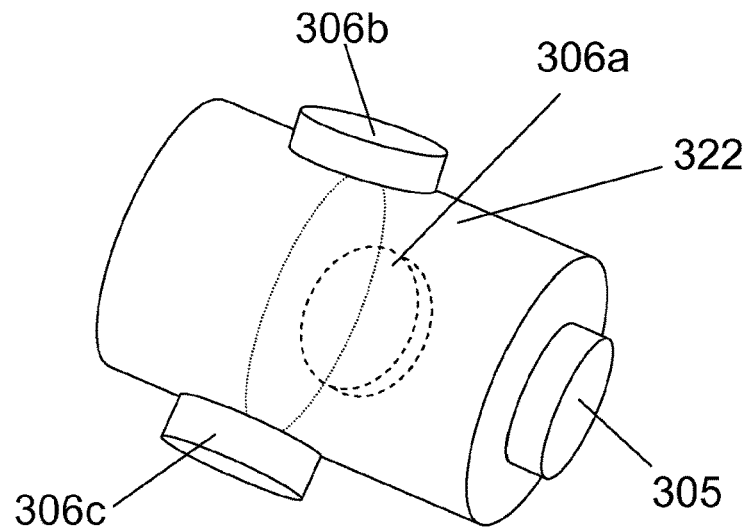

FIG. 5 shows a perspective view of a distal end 322 of an interventional device, with a forward looking ultrasound transducer 305 and three sideward looking ultrasound transducers 306a-c.

Figure 6:
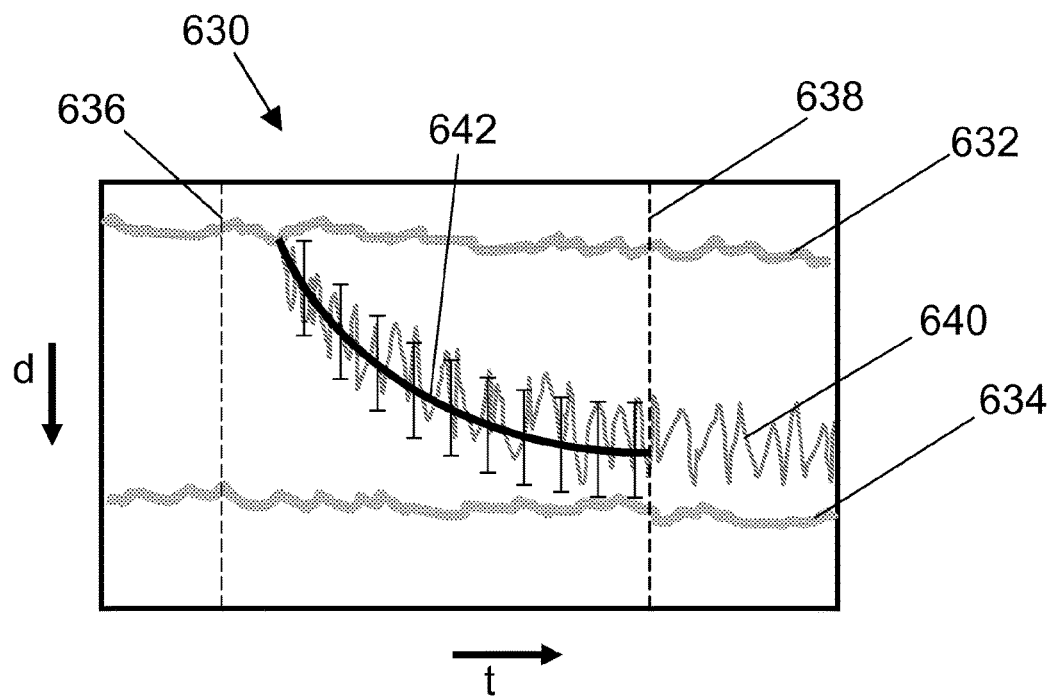
FIGS. 6-7 show stylized and real examples of an M-mode image.

FIG. 6 shows an example of an M-mode image 630. The M-mode image is an image which is composed by placing a plurality of A-lines. An A-line is known in the art and is a 1-dimensional representation of the information gained from each ultrasound transducer for a point in time. The M-mode image is known in the art, and is composed by placing a plurality of A-lines, which have been collected at monotonically increasing points in time, next to each other, so as to visualize changes over time. In FIG. 6, the A-lines, which are resolved by a depth d, are vertical lines placed next to each other so as also enable visualizing a progress in time t. The M-mode image 630 thus shows depth d on the vertical axis, and time t on the horizontal axis. The image shows an associated tissue with an anatomical structure with cardiac front wall 632 and cardiac back wall 634. At a point in time, start time 636, an ablation procedure starts, and it can be seen that lesion formation is starting shortly thereafter and progression towards, larger depth with time. The lesion is seen as the relatively noisy signal 640 which can be averaged to obtain a smoother indicator 642 for lesion progression. Once the lesion has reached an acceptable depth, the lesion procedure is stopped as indicated at the end time 638.

Figure 7:
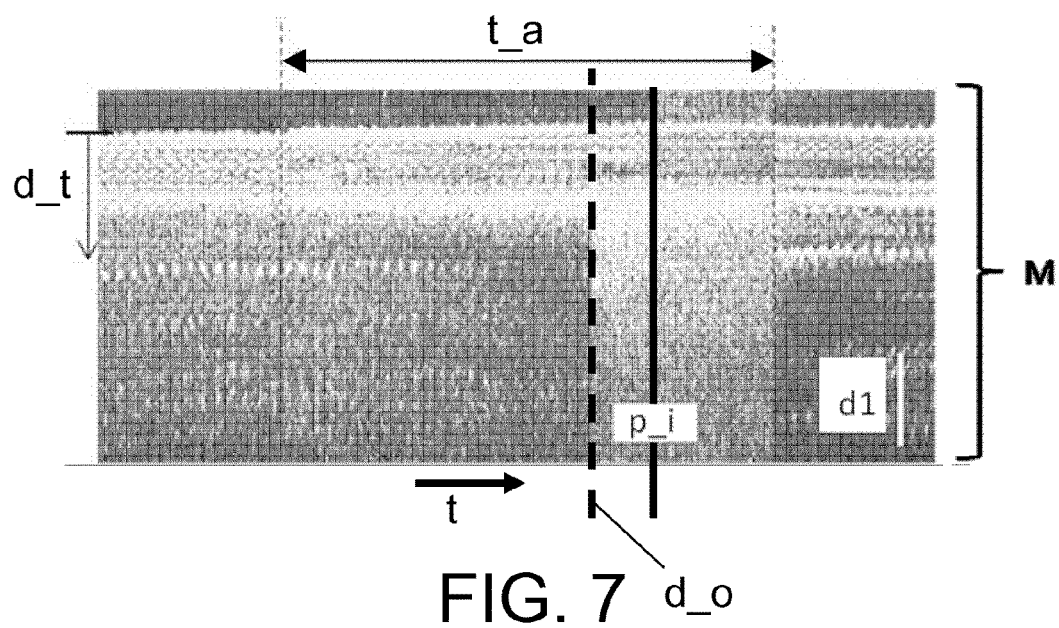

FIG. 7 shows an example of real experimental data from an open-chest sheep model. Radio frequency energy was delivered epicardially to create lesions that were simultaneously monitored with ultrasound and electrical impedance change. The ultrasound measurements are visualized in a so-called M-mode image M. The RF energy dissipated per time interval is 9 watt during the 20 second period denoted by t_a. The tissue depth in the M-mode image M is denoted by d_t. The absolute scale of the M-mode image is indicated by the scale bar denoted by d1, the scale bar corresponds to 1 millimeter. The solid line denoted p_i indicates the incidence of a tissue pop, the dashed line denoted d_o indicate the onset of changes in ultrasound that precede the pops. The figure shows that changes in the ultrasound measurements were detectable several seconds before tissue pops.

Figure 8:
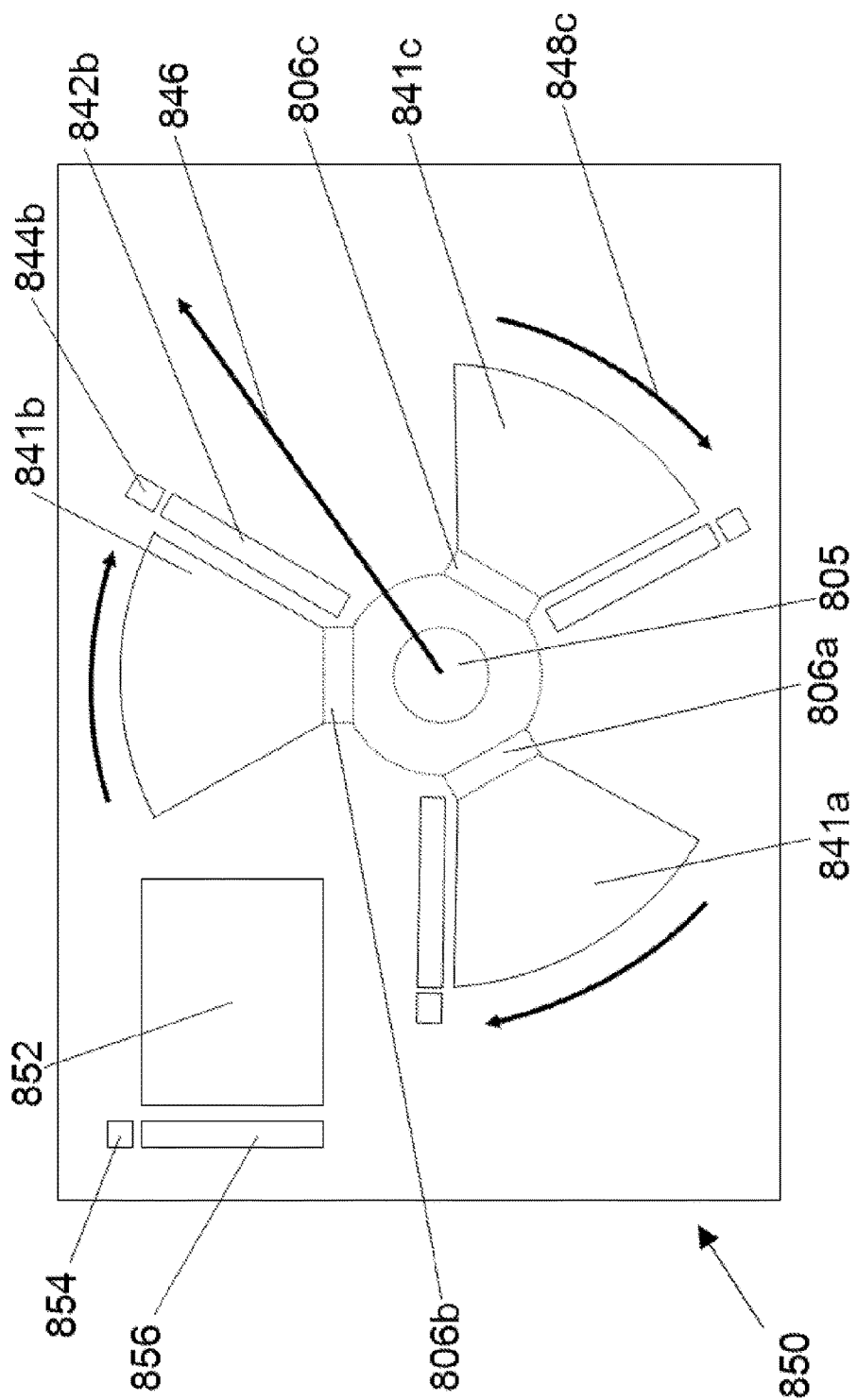
FIGS. 8-11 show exemplary graphical interfaces of display devices.

FIG. 8 shows an exemplary display device which has received ultrasound information packages from a plurality of ultrasound transducers, such as a the plurality of ultrasound transducers of FIGS. 3-5, and wherein the display device has a graphical interface 850 with the spatially different ultrasound display regions 841a-c corresponding to the ultrasound transducers 306a-c in FIGS. 3-5 which are also indicated by the regions 806a-c with dotted lines. The figure shows, that the relative spatial position of the different ultrasound display regions 841a-c match the corresponding relative spatial positions of the different adjacent tissue sample regions, which are placed in front of the respective ultrasound transducers. In the depicted example, the different ultrasound display regions 841a-c shows M-mode images, each with a depth axis which extends radially outwards, as indicated by arrow 846 and a time axis which extends tangentially as indicated by the curved arrows, such as arrow 848c. In an alternative embodiment, the M-mode images might be arranged so that the individual A-lines remain parallel (in a manner similar to the example depicted in FIG. 10). An advantage of having the A-lines parallel might be that similar differences in time is represented similarly (when depicted), regardless of the distance to the transducer. In the present example, the M-mode images are thus building up in time in a clock-wise fashion. The graphical interface 850 of the display device furthermore has regions showing A-lines (which are depicted at high framerate), such as region 842b, and tissue contact indicators, such as region 844b, which change color depending on the level of tissue contact between an ultrasound transducer and the associated tissue. The graphical interface 850 of the display device furthermore has an M-mode region 852 showing an M-mode image obtained by the forward looking ultrasound transducer, corresponding to ultrasound transducer 305 in FIGS. 3-5 (and also indicated in the graphical interface as region 805), an A-line region 856 showing an A-line obtained by the forward looking ultrasound transducer, and a contact indicator region 854 which changes color depending on a level of tissue contact between the forward looking transducer and the associated tissue sample.

Figure 9:
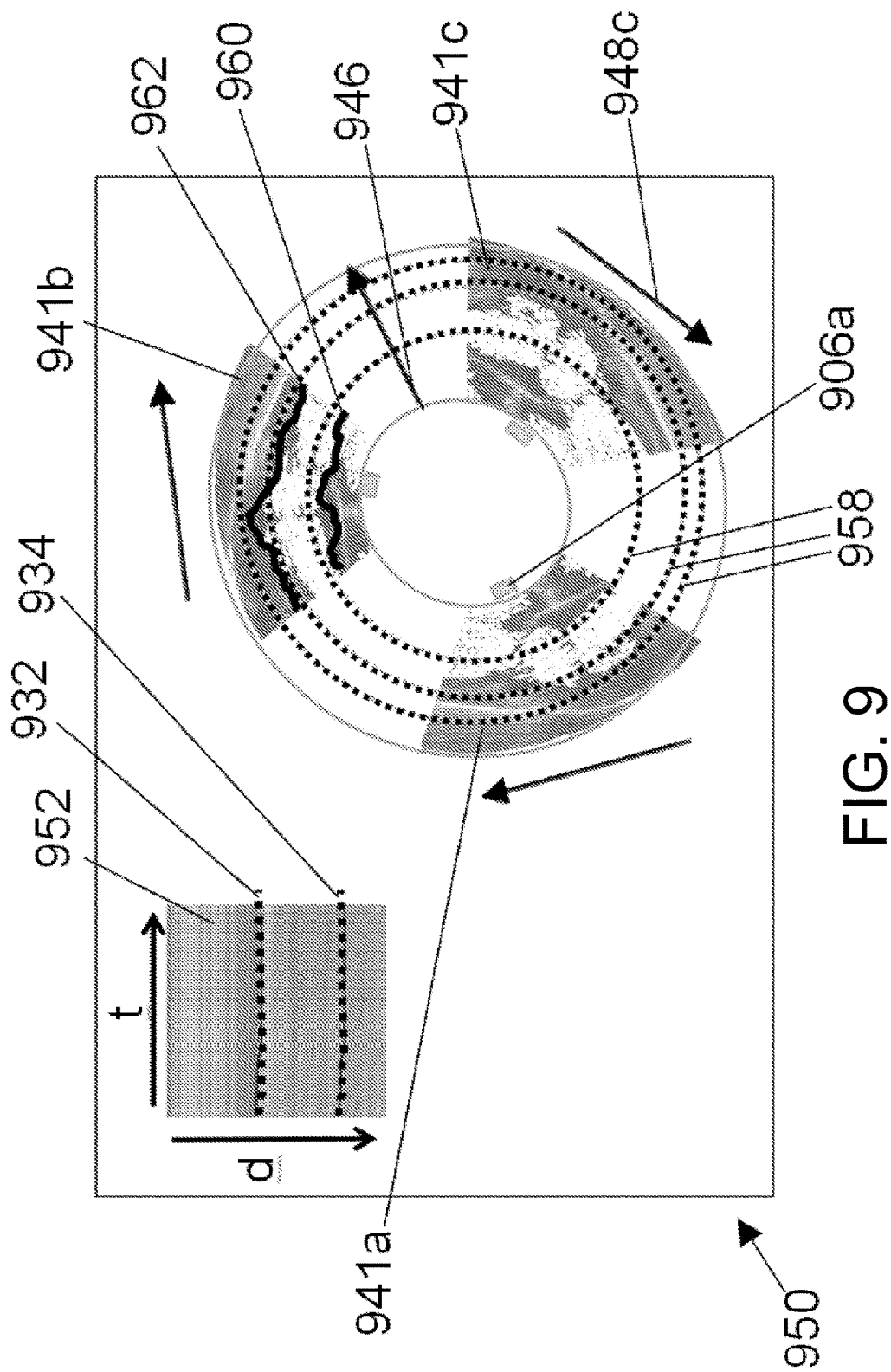

FIG. 9 shows another exemplary display device, similar to the display device of FIG. 8, with a graphical interface 950 with the spatially different ultrasound display regions 941a-c corresponding to the ultrasound transducers indicated, such as by region 906a. The relative spatial positions of the different ultrasound display regions 941a-c match the corresponding relative spatial positions of the different adjacent tissue sample regions. As in FIG. 8 the different ultrasound display regions 941a-c shows M-mode images which are inserted in FIG. 9, each with a depth axis which extends radially outwards, as indicated by arrow 946 and a time axis which extends tangentially as indicated by the tangentially oriented arrows, such as arrow 948c. An M-mode region 952 shows an M-mode image obtained by the forward looking ultrasound transducer, corresponding to ultrasound transducer 305 in FIGS. 3-5. The M-mode region 952 is also shown with time t and depth d on the axes. Furthermore, in the data depicted in the M-mode region 952 a front wall and back wall of an associated tissue with an anatomical structure has been detected and is indicated as line 932 and 934, respectively. Similarly, lines 960, 962 in ultrasound display region 941*b* indicate front- and back walls, respectively, of an anatomical structure adjacent to the ultrasound transducer corresponding to 305*b* in FIGS. 3-5.

Note also the fact that representing the spatially different ultrasound display regions 941*a-c*, which in the present example are M-mode images, according to the invention can actually provide new information because the observer can link a tissue feature seen in an individual image with features seen in other images. For example, the lines 960, 962 which indicate front- and back walls, respectively, in the ultrasound display regions 941*b* of FIG. 9, may be linked to corresponding lines in the other M-mode images (i.e., ultrasound display regions 941*a*, 941*c*). In other words, a possible advantage of the invention may be that an observer can better use the existing information in the images (when given the 'context' in the other images). Another possible advantage of the invention may that the observer is enabled to "guess" an existence and/or location of features in non-imaged regions between the images.

Figure 10:
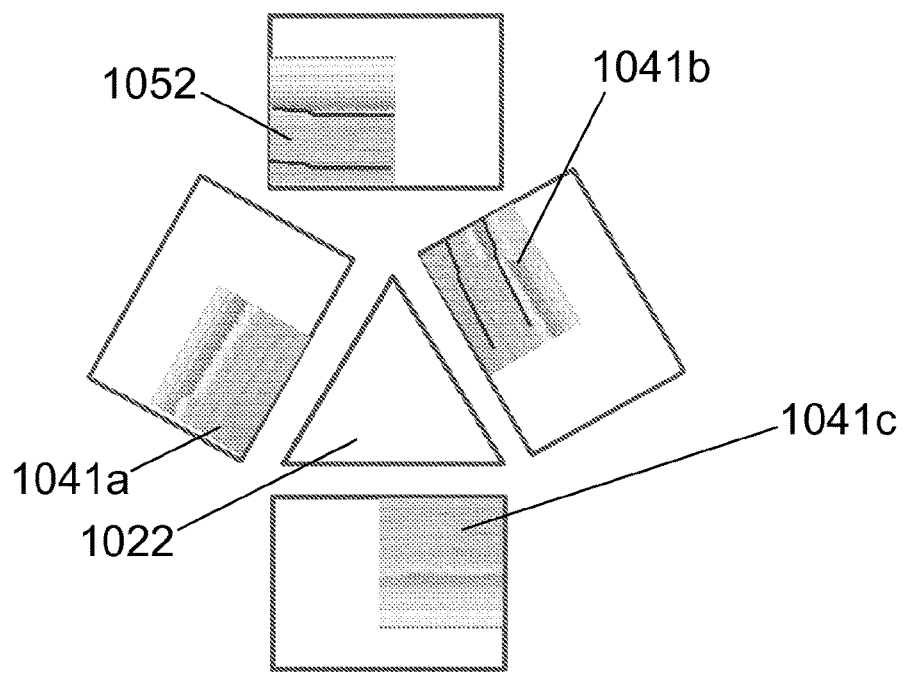

FIG. 10 shows yet another example of a display device, similar to the display device of FIG. 8, with graphical interfaces with the spatially different ultrasound display regions 1041*a-c* corresponding to the ultrasound transducers 306*a-c* of FIGS. 3-5. An M-mode region 1052 shows an M-mode image obtained by the forward looking ultrasound transducer, corresponding to ultrasound transducer 305 in FIGS. 3-5 is also shown with time t and depth d on the axes. The triangle 1022 is indicative of a position of the tip of the interventional device 322 in FIGS. 3-5 relative to the imaged regions of the associated tissue sample.

Figure 11:
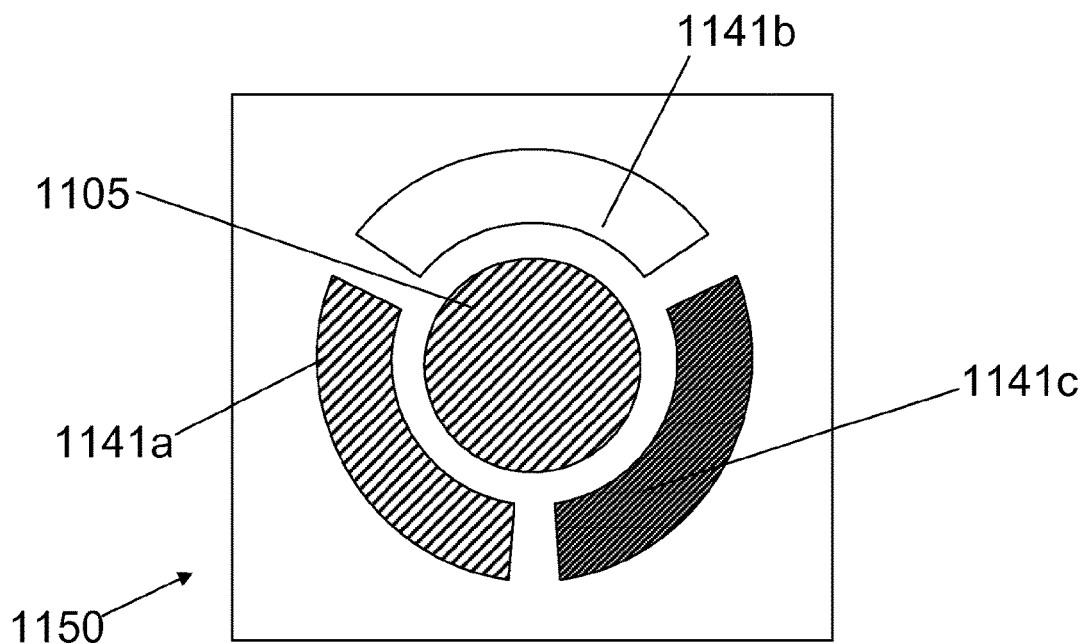

FIG. 11 shows an example of a graphical interface 1150 of a display device which shows which of the ultrasound imaging transducers of an interventional device as in FIGS. 3-5 are in good, intermediate or bad contact with the tissue. The graphical interface 1150 has regions 1141*a-c* which each are arranged for indicating whether the tissue contact between, respectively, ultrasound transducers 306*a-c* and an adjacent associated tissue sample is good (as indicated by the dark coloring of region 1141*c*), intermediate (as indicated by the dark-grey coloring of region 1141*a*) or bad (as indicated by the light coloring of region 1141*b*). Furthermore, a region 1105 in the middle is arranged for indicating whether the tissue contact between the forward looking ultrasound transducer 305 is good, intermediate or bad, and in the present example indicates that it is intermediate.

Figure 12:
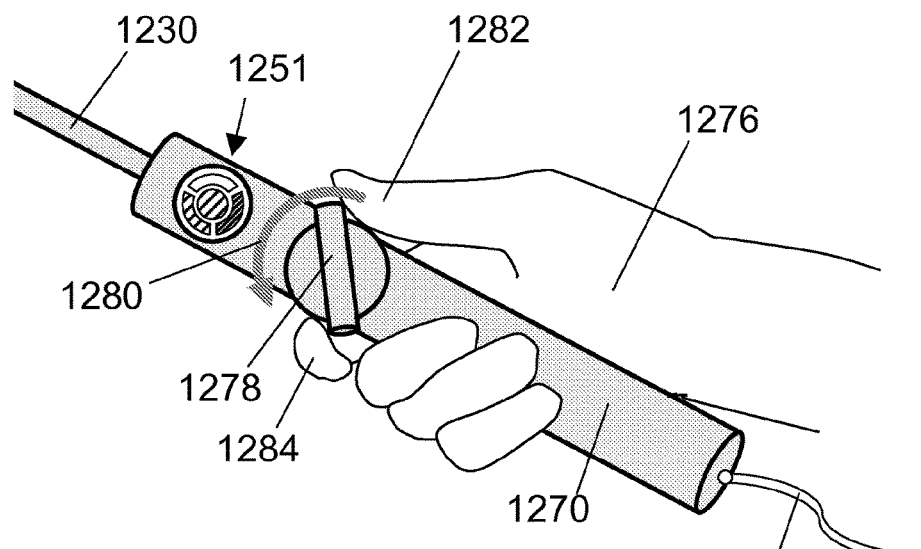
FIG. 12 shows a handle of an RF-ablation catheter.

FIG. 12 shows a handle 1270 of an RF-ablation catheter with an integrated display device 1251 with a graphical interface, such as a display (similar to graphical interface 1150 of FIG. 5), to indicate tissue contact. The handle is connected to a sample arm 1230 which has at its distal end an interventional device (not shown) with a distal end as in FIGS. 3-5. The handle has in its other end a cable 1274 for supplying power and for connecting to a processor for controlling the ultrasound transducers and for collecting the ultrasound information packages. The handle furthermore has a knob 1278 which can be turned (as indicated by arrow 1280) to control an ablation procedure. The handle 1270 is shown held in a human hand 1276 which controls the rotation of the knob 1278 with the thumb 1282 and index finger 1284.

Indication of tissue contact is very important to generate a successful ablation lesion. Using the ultrasound signal it is possible to 'see' tissue contact and using software algorithms to assess the quality of the contact between the ultrasound imaging transducer and the tissue. Visual feedback is an option to show contact quality to the clinician, but audio or tactile feedback is also a possibility.

Secondly the algorithm which assesses the tissue contact can be used to decide which ultrasound M-mode image should be displaced or enlarged.

Figure 13:
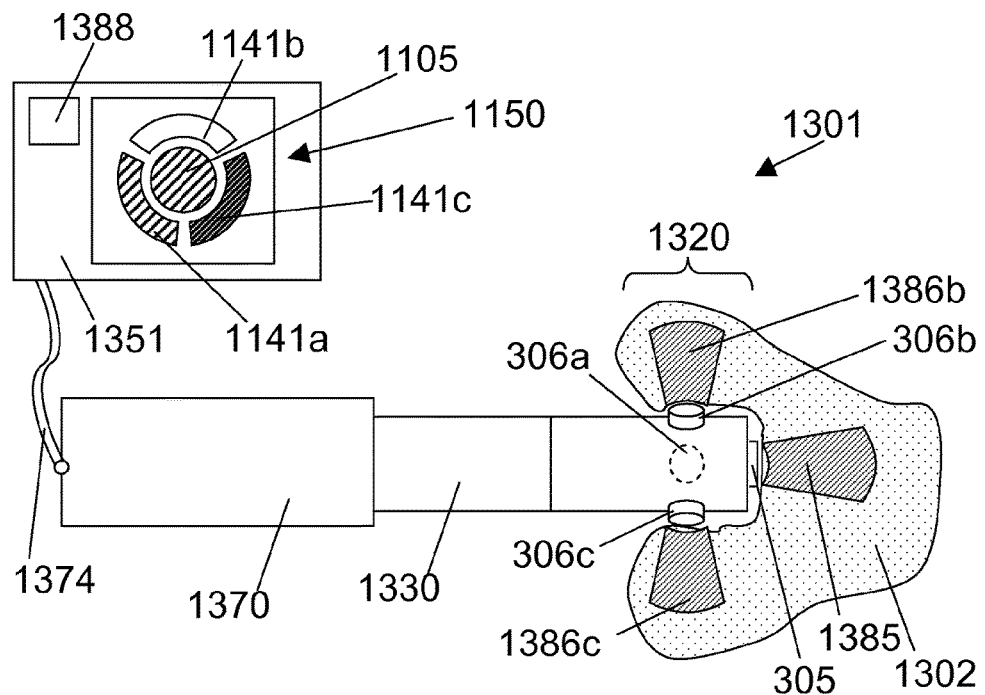
FIG. 13 shows an examination system.

FIG. 13 shows an examination system 1301 for examining an associated tissue sample 1302, the examination system comprising an interventional device 1320 comprising:

a plurality of ultrasound transducers 306*a-c*, wherein different ultrasound transducers within the plurality of ultrasound transducers are arranged to obtain ultrasound information packages from spatially different adjacent tissue sample regions 1386*b-c* when the associated tissue sample is placed adjacent the plurality of ultrasound transducers, a display device 1351 arranged for receiving and visualizing the ultrasound information packages in spatially different ultrasound display regions 1141*a-c* on the display device 1351, wherein the relative spatial positions of the different ultrasound display regions match the corresponding relative spatial positions of the different adjacent tissue sample regions 1386*b-c*. The figure further shows a sample arm 1330 which has at its distal end the interventional device, the sample arm being attached at its proximal end to a handle 1370, a cable 1374 for supplying power and for connecting to a processor 1388 for controlling the ultrasound transducers and for collecting the ultrasound information packages, the processor being positioned in a display device 1351. The figure furthermore shows an adjacent tissue sample region 1385 being imaged by the forward looking ultrasound transducer 305.

Figure 14:
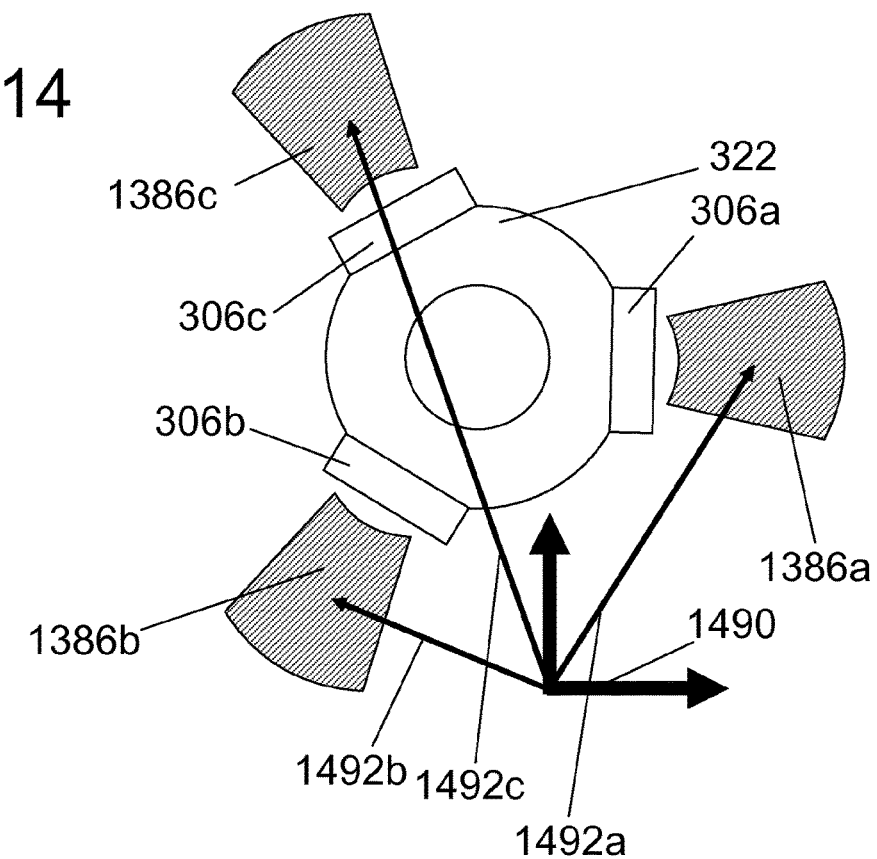
FIGS. 14-15 show a first set of vectors and a second set of vectors.
Figure 15:
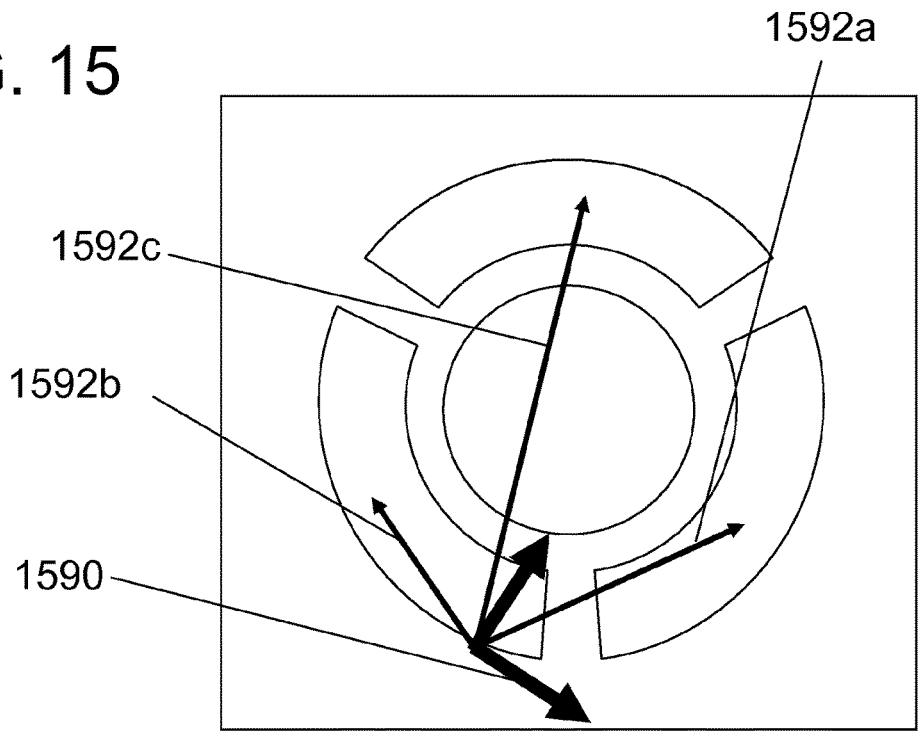

FIGS. 14-15 show that the relative spatial positions of the different ultrasound display regions match the corresponding relative spatial positions of the different adjacent tissue sample regions 1386*a-c*.

FIG. 14 shows a first set of vectors 1492*a-c* in a coordinate system 1490 which define the positions of the different adjacent tissue sample regions 1386*a-c* as imaged with an interventional device as depicted in FIGS. 3-5.

FIG. 15 shows that the relative spatial positions of the different ultrasound display regions (reference signs are left out for clarity, but the figure shows a graphical interface similar to the graphical interface of FIG. 11) match the corresponding relative spatial positions of the different adjacent tissue sample regions 1386*a-c* (of FIG. 14). In particular, it can be seen that a second set of vectors 1592*a-c* in a coordinate system 1590 is similar to the first set of vectors, although it has been rotated and scaled. It is also envisioned, that the invention encompasses embodiments where the second set of vectors has been stretched, such as scaled differently in different directions.

Figure 16:
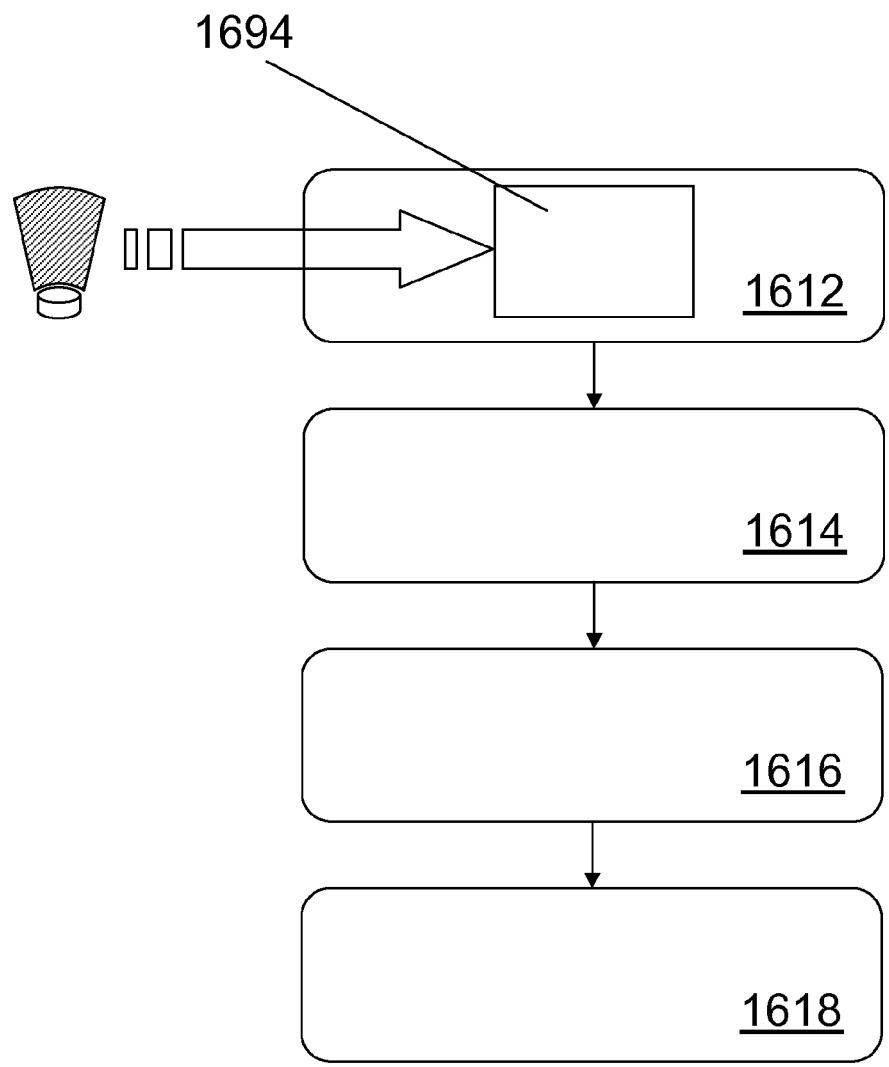
FIG. 16 is a flow chart of a method.

FIG. 16 is a flow chart of a method for organizing a display device 1351 and for visualizing information obtained from a plurality of ultrasound transducers 306*a-c*, the method comprising:

obtaining 1612 a first number of ultrasound information packages 1694 where different ultrasound information packages comprise information from spatially different adjacent tissue sample regions 1386*a-c*, obtaining 1614 relative spatial positions of the corresponding different adjacent tissue sample regions, determining 1616 a second number of relative spatial positions of different ultrasound display regions 1141a-c on the display device 1351, visualizing 1618 the ultrasound information packages in the spatially different ultrasound display regions 1141a-c, wherein the first number is equal to the second number and wherein the relative spatial positions of the different ultrasound display regions match the corresponding relative spatial positions of the different adjacent tissue sample regions.

Figure 17:
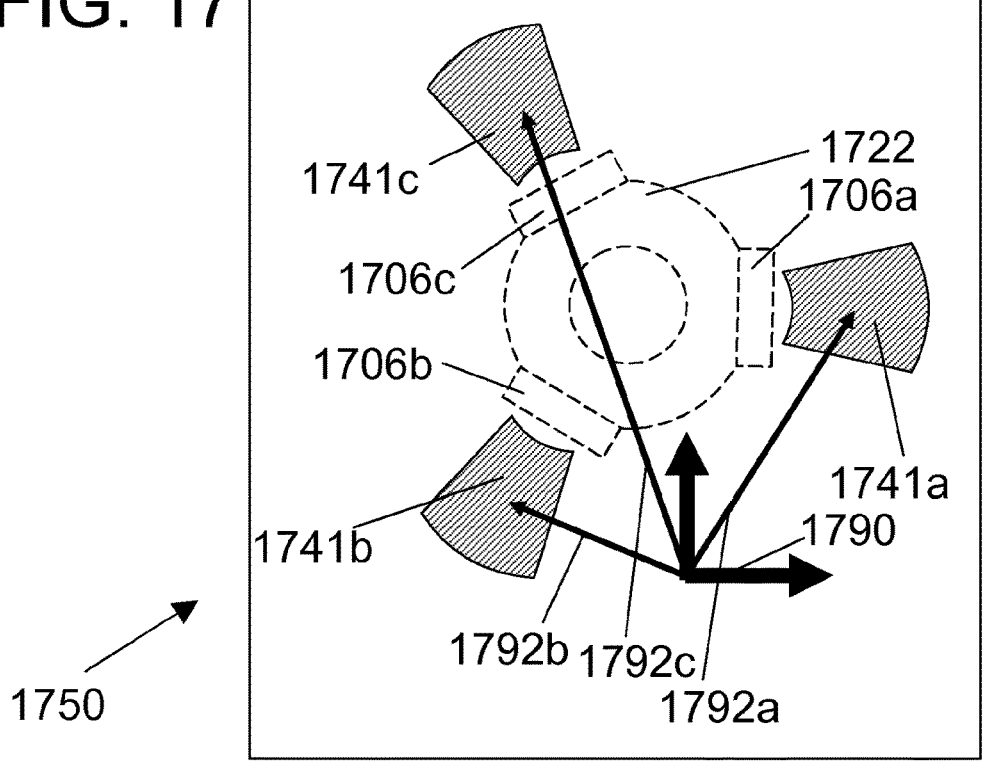
FIGS. 17-18 show graphical interfaces of a display device.

FIG. 17 shows a graphical interface 1750 of a display device showing the spatially different ultrasound display regions 1741a-c corresponding to the ultrasound transducers 306a-c in FIGS. 3-5 which are also indicated by the regions 1706a-c with dotted lines. The figure also shows a second set of vectors 1792a-c in a coordinate system 1790 which define the positions of the different ultrasound display regions 1741a-c corresponding to different adjacent tissue sample regions as imaged with an interventional device as depicted in FIG. 14. It is noted that the relative orientation of each of the different ultrasound display regions around an axis through the middle of the ultrasound display region matches the relative orientation of the adjacent tissue sample regions around their respective axes (where each axis is an axis through the center of the respective ultrasound display region which axis is orthogonal to the plane of the paper).

Figure 18:
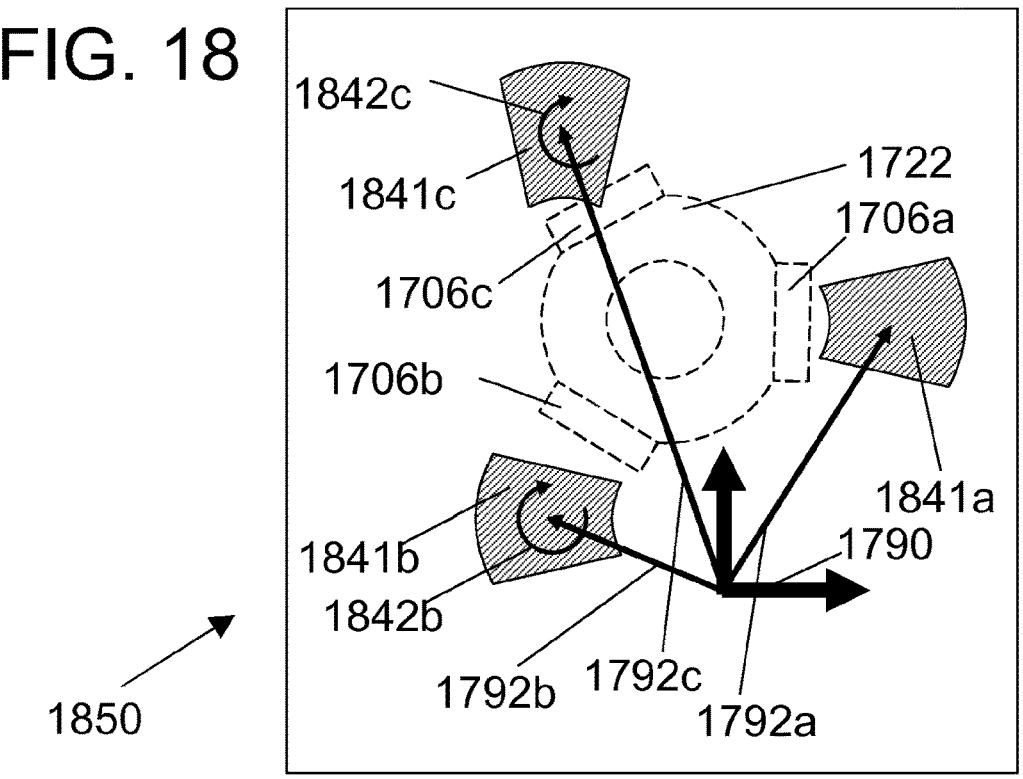

FIG. 18 shows a graphical interface 1850 of a display device showing the spatially different ultrasound display regions 1841a-c. The figure also shows a second set of vectors 1792a-c in a coordinate system 1790 which define the positions of the different ultrasound display regions 1841a-c. Note that the second set of vectors is identical to the second set of vectors of FIG. 17. However, it is noted that the relative orientation of each of the different ultrasound display regions around an axis through the middle of the ultrasound display region does not match the relative orientation of the adjacent tissue sample regions around their respective axes, in particular the relative orientation of ultrasound display region 1841a matches the orientation of the corresponding adjacent tissue sample region, the relative orientation of ultrasound display region 1841b is angled 60 degrees clockwise (as indicated by arrow 1842b) with respect to the orientation of the corresponding adjacent tissue sample region, and the relative orientation of ultrasound display region 1841c is angled 30 degrees clockwise (as indicated by arrow 1842c) with respect to the orientation of the corresponding adjacent tissue sample region. The rotation of each of the ultrasound display region may be determined by observing the rotation in relation to the corresponding position vector.

To sum up, the present invention relates to an examination system 1301 for examining an associated tissue sample 1302, where the examination system comprises an interventional device 1320 which comprises a plurality of ultrasound transducers 306a-c and wherein the different ultrasound transducers are arranged to obtain images of different regions of an associated tissue sample, and wherein the examination system furthermore comprises a display device 1351 arranged for showing the images so that each of their positions corresponds to the corresponding positions of the different adjacent tissue sample regions in the associated tissue sample. A possible advantage of the system may be, that relevant information regarding the associated tissue sample is conveyed to an observer in a fast an intuitive manner.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. An examination system for examining an associated tissue sample, the examination system comprising
an interventional device comprising:
a plurality of ultrasound transducers, wherein different ultrasound transducers within the plurality of ultrasound transducers are arranged to obtain ultrasound information packages from spatially different adjacent tissue sample regions when the associated tissue sample is placed adjacent the plurality of ultrasound transducers,
a display device arranged for receiving and visualizing the ultrasound information packages in spatially different ultrasound display regions on the display device, the spatially different display regions configured to display M-mode images, each of the M-mode images being arranged with one of (i) a depth axis extending radially outwards and a time axis extending tangentially to the depth axis or (ii) parallel individual A-lines,
wherein relative spatial positions of the spatially different ultrasound display regions match corresponding relative spatial positions of the spatially different adjacent tissue sample regions,
and wherein the examination system further comprises a processor arranged for determining tissue contact information packages based on the ultrasound information packages, wherein the tissue contact information packages are indicative of a level of tissue contact between the interventional device and the associated tissue sample at ultrasound transducer positions.

2. An examination system according to claim 1 wherein a relative orientation of each of the spatially different ultrasound display regions around an axis through the middle of the ultrasound display region matches a relative orientation of the adjacent tissue sample regions around their respective axes.

3. An examination system according to claim 1 wherein the display device is arranged for receiving and visualizing the tissue contact information packages in spatially different tissue contact display regions of the display device, and
wherein the relative spatial positions of the spatially different tissue contact display regions are similar to the relative spatial positions of the tissue contact sensor positions.

4. An examination system according to claim 1, wherein the display device is further arranged for indicating the position of any one of the predetermined features on the display.

5. An examination system according to claim 1, wherein the interventional device is any one of an endoscope, a catheter, a biopsy needle.

6. An examination system according to claim 1, wherein the plurality of ultrasound transducers comprises at least 3 different ultrasound transducers.

7. An examination system according to claim 1, wherein a coordinate position of at least one ultrasound transducer within the plurality of ultrasound transducers is determined with respect to a fixed coordinate system.

8. An examination system according to claim 7, wherein the relative spatial positions of the spatially different ultrasound display regions is based on said coordinate position.

9. An examination system according to claim 1, wherein the plurality of ultrasound transducers is positioned and oriented so as to enable imaging of spatially different adjacent tissue sample regions being positioned around the interventional device.

10. An examination system according to claim 1 wherein the interventional device and the display device are attached to a handle.

11. Use of an examination system according to claim 1 for examining an associated tissue sample.

12. A method for organizing a display device and for visualizing information obtained from a plurality of ultrasound transducers at a plurality of ultrasound transducer positions, the method comprising:
obtaining a first number of ultrasound information packages where different ultrasound information packages comprise information from spatially different adjacent tissue sample regions,
obtaining relative spatial positions of a corresponding different adjacent tissue sample regions,
determining a second number of relative spatial positions of different ultrasound display regions on the display device,
displaying the ultrasound information packages in spatially different ultrasound display regions, the spatially different display regions configured to display M-mode images, each of the M-mode images being arranged one of (i) a depth axis, extending radially outwards and a time axis extending tangentially to the depth axis or (ii) parallel individual A-lines,
wherein the first number is equal to the second number and wherein the relative spatial positions of the spatially different ultrasound display regions match a corresponding relative spatial positions of the different adjacent tissue sample regions, and
determine tissue contact information packages based on the ultrasound information packages, wherein the tissue contact information packages are indicative of a level of tissue contact between an interventional device and an associated tissue sample at ultrasound transducer positions.

13. A non-transitory computer readable storage medium comprising a computer program wherein the computer program when executed on a computer is adapted to enable the computer to operate a processor arranged for:
receiving a first number of ultrasound information packages where different ultrasound information packages comprise information from spatially different adjacent tissue sample regions,
receiving relative spatial positions of the different adjacent tissue sample regions,
determining a second number of relative spatial positions of different ultrasound display regions on a display device,
displaying the ultrasound information packages in the spatially different ultrasound display regions, the spatially different display regions configured to display M-mode images, each of the M-mode images being arranged with: one of (i) a depth axis, extending radially outwards and a time axis extending tangentially to the depth axis or (ii) parallel individual A-lines,
wherein the first number is equal to the second number and wherein the relative spatial positions of the spatially different ultrasound display regions match a corresponding relative spatial positions of the different adjacent tissue sample regions, and
determine tissue contact information packages based on the ultrasound information packages, wherein the tissue contact information packages are indicative of a level of tissue contact between an interventional device and an associated tissue sample at ultrasound transducer positions.

14. The non-transitory computer readable storage medium according to claim 13, wherein a relative orientation of each of the spatially different ultrasound display regions around an axis through the middle of the ultrasound display region matches a relative orientation of the adjacent tissue sample regions around their respective axes.

* * * * *